(12) United States Patent
Graf

(10) Patent No.: US 7,691,131 B2
(45) Date of Patent: Apr. 6, 2010

(54) INTERVERTEBRAL CONNECTING DEVICE

(75) Inventor: Henry Graf, Lyons (FR)

(73) Assignee: Sofamor S.N.C. (FR)

( * ) Notice: Subject to any disclaimer, the term of this patent is extended or adjusted under 35 U.S.C. 154(b) by 2179 days.

(21) Appl. No.: 10/330,722

(22) Filed: Dec. 27, 2002

(65) Prior Publication Data

US 2003/0153912 A1    Aug. 14, 2003

Related U.S. Application Data

(63) Continuation of application No. PCT/FR01/02098, filed on Jun. 29, 2001.

(30) Foreign Application Priority Data

Jun. 30, 2000 (FR) .................................. 00 08522
Aug. 1, 2000 (FR) .................................. 00 10155

(51) Int. Cl.
*A61B 17/70* (2006.01)
(52) U.S. Cl. ................................................... 606/256
(58) Field of Classification Search .................. 606/61, 606/72, 73, 287–288, 295, 246–279, 300–301, 606/305–308, 319, 321–322, 325, 328; 623/23.4; 403/56, 76, 90, 114, 122
See application file for complete search history.

(56) References Cited

U.S. PATENT DOCUMENTS

| | | | | |
|---|---|---|---|---|
| 2,531,892 A | * | 11/1950 | Reese | ........................... 403/11 |
| 3,003,399 A | * | 10/1961 | Donner | ...................... 89/37.13 |
| 3,013,244 A | * | 12/1961 | Rudy | ........................... 439/777 |
| 3,795,922 A | * | 3/1974 | Herbert et al. | ........... 623/20.22 |
| 4,946,458 A | * | 8/1990 | Harms et al. | ................... 606/61 |
| 5,057,111 A | * | 10/1991 | Park | .............................. 606/69 |
| 5,501,684 A | * | 3/1996 | Schlapfer et al. | .............. 606/73 |
| 5,536,268 A | * | 7/1996 | Griss | ........................... 606/61 |
| 5,549,681 A | * | 8/1996 | Segmuller et al. | .......... 623/23.4 |
| 5,569,247 A | * | 10/1996 | Morrison | ...................... 606/61 |
| 5,591,166 A | * | 1/1997 | Bernhardt et al. | ............. 606/61 |
| 5,672,176 A | | 9/1997 | Biedermann et al. | |
| 5,683,392 A | | 11/1997 | Richelsoph et al. | |
| 5,690,630 A | | 11/1997 | Errico et al. | |
| 5,725,528 A | * | 3/1998 | Errico et al. | ................... 606/61 |
| 5,733,285 A | | 3/1998 | Errico et al. | |
| 5,735,853 A | * | 4/1998 | Olerud | ......................... 606/71 |
| 5,797,911 A | * | 8/1998 | Sherman et al. | ............... 606/61 |
| 5,797,912 A | * | 8/1998 | Runciman et al. | ............. 606/69 |
| 6,022,350 A | * | 2/2000 | Ganem | ........................ 606/272 |
| 6,050,997 A | * | 4/2000 | Mullane | ....................... 606/61 |

(Continued)

FOREIGN PATENT DOCUMENTS

WO        WO 00/15125        3/2000

*Primary Examiner*—Thomas C Barrett
*Assistant Examiner*—James L. Swiger

(57) ABSTRACT

The invention concerns a device comprising at least a fixed element (2), secured to a vertebra, at least a mobile element (10), capable of moving relative to the or each fixed element, and at least an intermediate element (22) for articulating the mobile element relative to the fixed element. The intermediate element (22) is received in an internal volume of the mobile element % (10), and the fixed element (2) is received at least partly in an internal volume (26) of the intermediate element (22). Means are provided for securing, at least in translation, said intermediate element (22) to the fixed element (2), comprising the periphery of the substantially rigid outlet of the internal volume of the intermediate element.

25 Claims, 13 Drawing Sheets

U.S. PATENT DOCUMENTS

| | | | |
|---|---|---|---|
| 6,113,601 A * | 9/2000 | Tatar | 606/266 |
| 6,273,914 B1 * | 8/2001 | Papas | 623/17.11 |
| 6,315,779 B1 * | 11/2001 | Morrison et al. | 606/281 |
| 6,610,062 B2 * | 8/2003 | Bailey et al. | 606/261 |
| 6,623,485 B2 * | 9/2003 | Doubler et al. | 606/61 |
| 6,884,241 B2 * | 4/2005 | Bertranou et al. | 606/261 |
| 6,887,242 B2 * | 5/2005 | Doubler et al. | 606/61 |
| 6,921,226 B2 * | 7/2005 | Rundle et al. | 403/77 |
| 7,229,443 B2 * | 6/2007 | Eberlein et al. | 606/69 |

\* cited by examiner

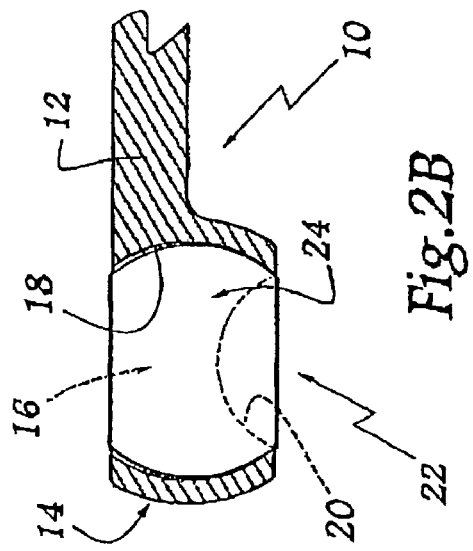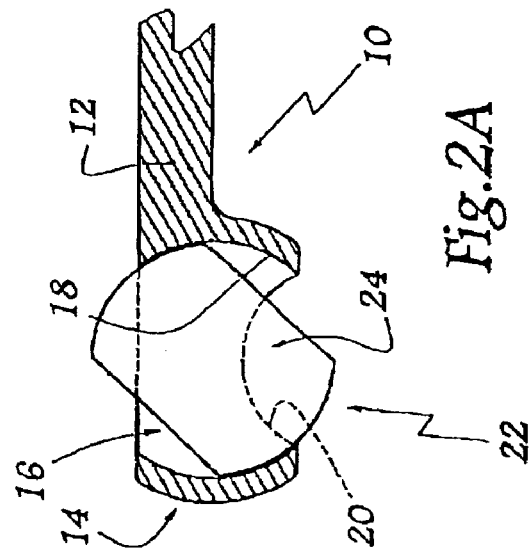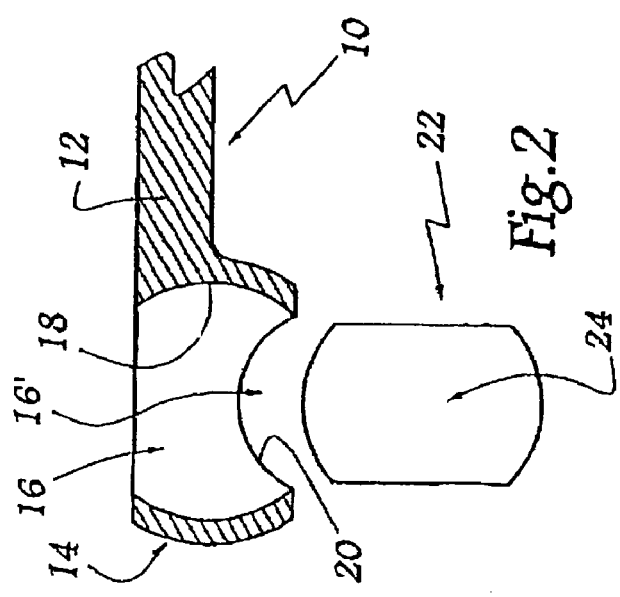

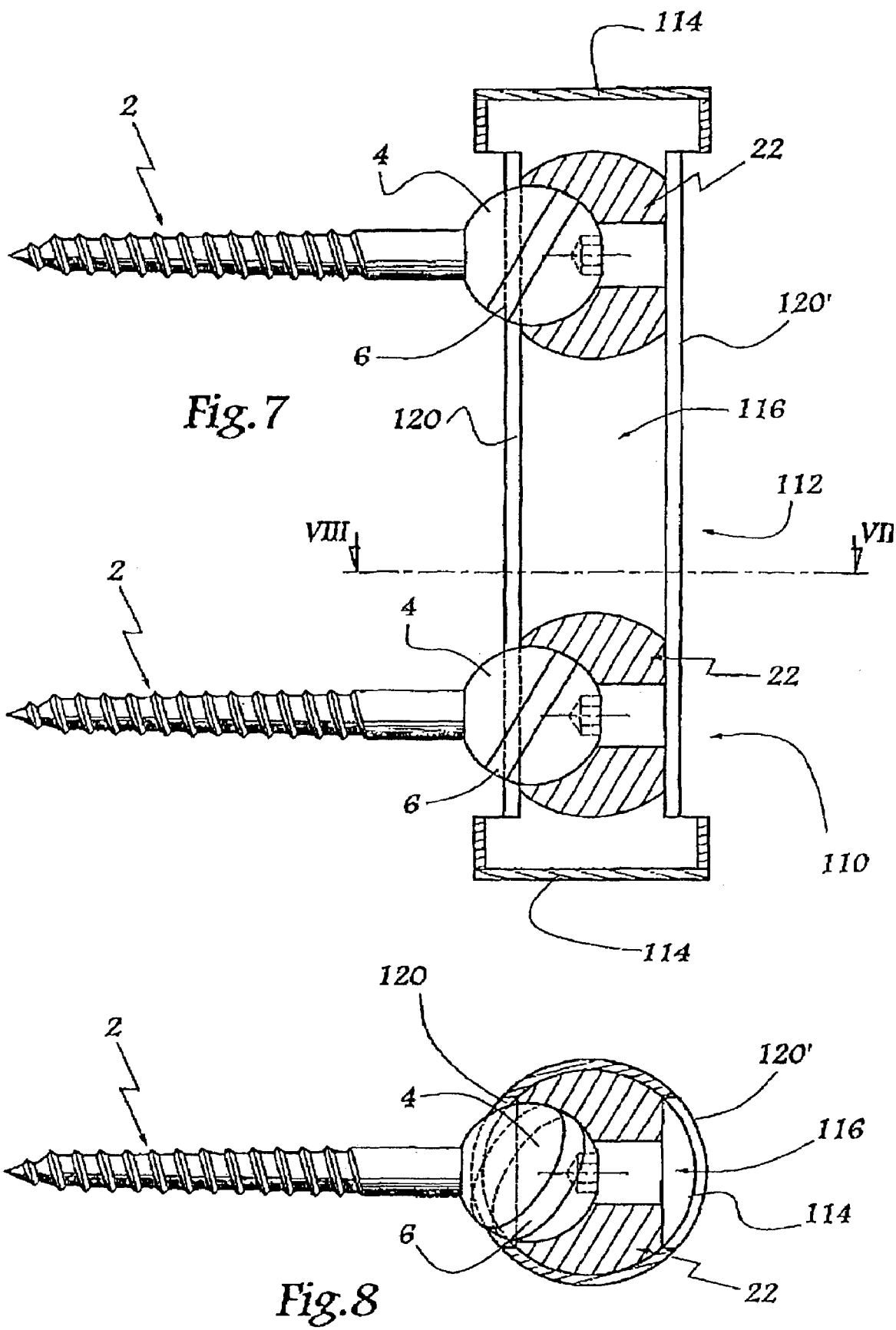

INTERVERTEBRAL CONNECTING DEVICE

CROSS REFERENCE TO RELATED APPLICATIONS

The present application is a continuation of International Patent Application No. PCT/FR01/02098 filed 29 Jun. 2001; and claims priority to French Patent Application Nos. 00/08522 filed 30 Jun. 2000 and 00/10155 filed 1 Aug. 2000; all of which are hereby incorporated by reference.

The present invention relates to an intervertebral connecting device.

BACKGROUND

A known device of this type exists, which has at least two pedicle screws, each of which has a first end connected with a corresponding vertebral body, a swollen intermediate portion, as well as a second threaded end. Auxiliary components, provided with a bow for attachment of a rod extending between the vertebrae, are arranged on each of the aforementioned swollen portions. A bolt, which cooperates with the threaded end of each screw, makes possible the immobilization of each auxiliary component, once the latter is positioned in the appropriate manner.

This known device nevertheless has certain disadvantages, in that it involves a relatively delicate assembly process. Furthermore, once implanted, it offers no degree of freedom between the different elements of which it consists. Thus, when forces are exerted on the vertebral bodies, this absence of degree of freedom induces a transmission of these forces over the whole device, so that the latter has a tendency to become disconnected from the vertebrae which it connects and furthermore induces malfunctionings with regard to the whole vertebral chain.

SUMMARY

In order to palliate these different disadvantages, the present invention proposes the execution of a device whose structure is simple, the assembly of which is easy and which is implanted in a reliable manner in the vertebrae which it connects.

To this effect, it relates to an intervertebral connecting device, which is intended to connect at least two vertebrae together, this device being characterized in that it includes:
  at least one stationary element, connected with a vertebra or with the sacrum,
  at least one mobile connecting element capable of moving with respect to the stationary element or each stationary element,
  as well as at least one intermediate element allowing the articulation of the mobile element or each mobile element with respect to the stationary element or each stationary element,
  in that the intermediate element or each intermediate element is received in an interior volume of said mobile element,
  in that the stationary element or the mobile element is received at least partially in an interior volume of the intermediate element,
  and in that it is provided with some means allowing the connection, at least in translation, of said stationary element or of said mobile element with respect to said intermediate element, these means of connection in translation including the periphery of the outlet, which is essentially rigid, of the interior volume of the intermediate element.

BRIEF DESCRIPTION OF THE FIGURES

The invention will be described below in reference to the appended drawings given only as non-limiting examples and in which:

FIGS. 2, 2A and 2B are views similar to FIG. 1, illustrating three steps of the assembly of an intermediate element of the device of FIG. 1, in the interior volume of a mobile element of this device;

FIGS. 7 and 8 are respectively views in longitudinal and cross section of a device according to an additional embodiment of the invention.

DESCRIPTION OF THE ILLUSTRATED EMBODIMENTS

Figure 1:
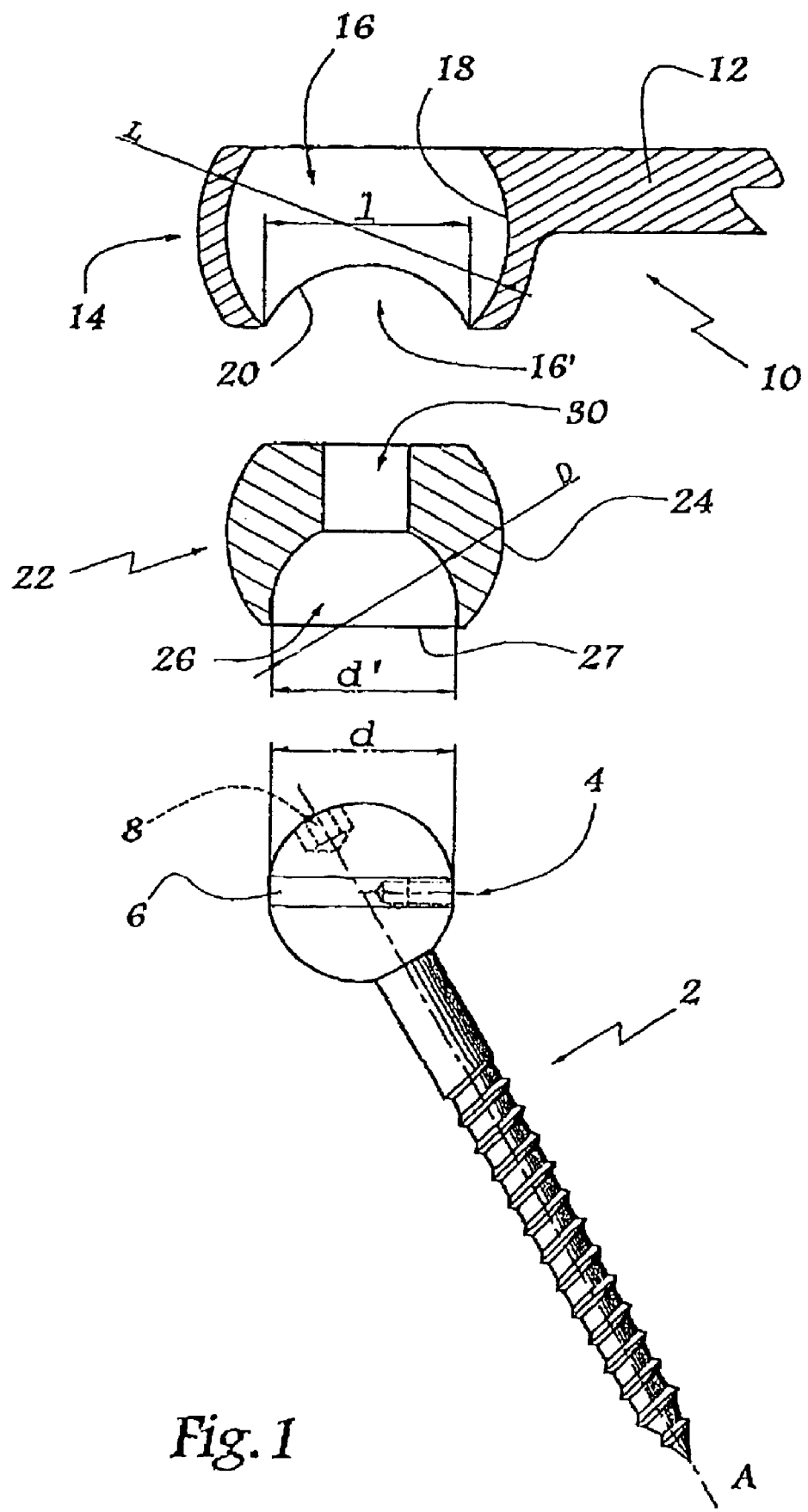
FIG. 1 is a view in longitudinal section, illustrating the different elements constituting an intervertebral connecting device according to a first embodiment of the invention.

FIG. 1 illustrates a first embodiment of the connecting device according to the invention, which includes pedicle screw 2, which is intended to be connected in a vertebral body which is not represented. This pedicle screw, which thus constitutes a stationary element, is provided with spherical head 4 which has equatorial flat part 6 extending in an inclined manner, in the sense that it is not perpendicular to main axis A of screw 2. Head 4 is furthermore hollowed with blind hole 8, intended for receiving a maneuvering component, in particular the end of a screwdriver which is not represented.

The device represented in FIG. 1 also includes a mobile element, which is illustrated partially and designated overall by the reference 10. This mobile element has body 12 which extends between the two vertebrae connected by the device of the invention and which is ended by two hollow ends, a single one of which, 14, is represented.

Each end defines housing 16, forming an interior volume of element 10, which is bordered by walls 18 forming a truncated sphere. These walls have notch 20 making it possible to locally widen the section of passage of housing 16 so as to allow introduction of the intermediate element, as will be described subsequently. Furthermore, the transverse dimension l of outlet 16' of housing 16 is less than the diameter L of this housing.

The device of FIG. 1 finally includes intermediate element 22, whose exterior surface 24 forms a portion of a sphere, whose diameter is identical to that L of housing 16. Intermediate element 22 is hollowed with an opening passing through, which defines housing 26, forming an interior volume bordered by truncated spherical walls, whose diameter D is identical to that of head 4. Housing 26 connects with chamber 30 allowing passage of the aforementioned maneuvering component, in the direction of blind hole 8.

The assembly of the device illustrated in FIG. 1 will be described in reference to FIGS. 2 and 3.

In a first step, it is a matter of introducing intermediate element 22 into interior volume 16 of mobile element 10. To this effect, this intermediate element 22 is arranged so that its spherical exterior surface 24 is in the vicinity of outlet 16'. Then, intermediate element 22 and mobile element 10 are axially brought together. The intermediate element and the mobile element are not connected in rotation or in translation in this position of introduction.

Intermediate element 22 is then pivoted around its axis so that its exterior surface 24 extends in the vicinity of interior walls 18, as shown in FIG. 2C. Once these operations are completed, intermediate element 22 has no degree of freedom in translation with respect to the mobile element, in this position of use. In effect, the transverse dimension 1 of outlet 16' is less than the exterior diameter of intermediate element 22. On the other hand, the latter has three degrees of freedom in rotation with respect to mobile element 10.

Figure 3A:
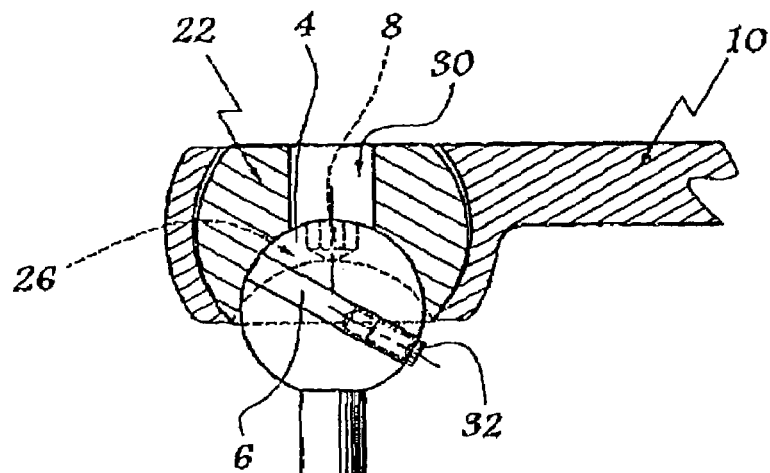
FIGS. 3 and 3A are views similar to FIG. 1, illustrating the introduction of a stationary element of the device of FIG. 1 into the interior volume of its intermediate element.
Figure 3:
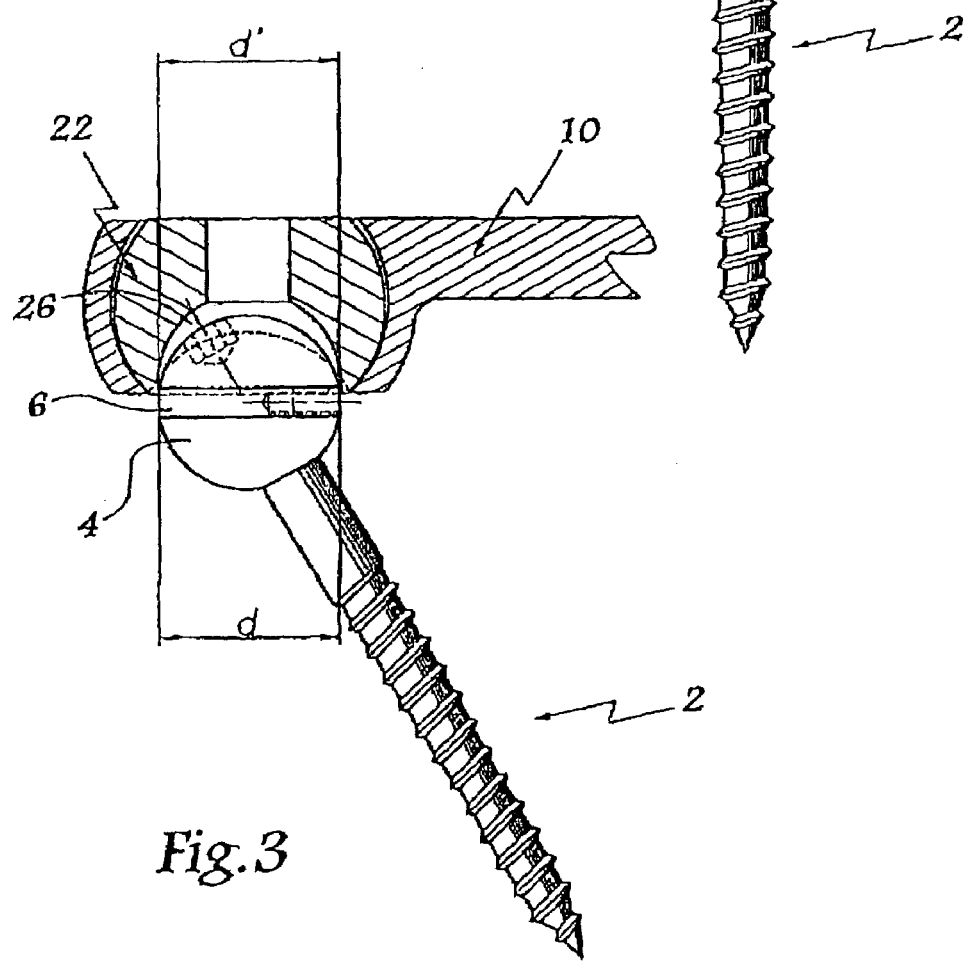

Then, as shown in FIG. 3, it is a matter of introducing spherical head 4 of pedicle screw 2 into housing 26 of intermediate element 22. To this effect, this screw 2 is first of all inclined so that flat part 6 extends horizontally in this FIG. 3, namely perpendicularly to the main axis of intermediate element 22.

This intermediate element 22 is then brought toward screw 2, according to a translation parallel to the main axis of this intermediate element 22. Given that the transverse dimension d of the flat part is equal to, or slightly less than, the transverse dimension d' of outlet 27 of housing 26, this allows free introduction of head 4 into this housing 26, which is illustrated in FIG. 3.

The periphery of outlet 27 is essentially rigid, that is to say non-deformable. To this effect, intermediate element 22 can be produced entirely out of a rigid material, metallic in particular. As a variant, this intermediate element can be produced out of a deformable material, such as polyethylene, a rigid ring then being connected in the vicinity of this outlet.

Then, head 4 is pivoted inside of the housing so that flat part 6 is inclined again, that is to say that it is no longer facing the aforementioned outlet 27. Head 4 is then free to pivot with respect to this housing 26 but has no degree of freedom in translation with respect to intermediate element 22, given that diameter D of head 4 is greater than the transverse dimension of outlet 27 of housing 26.

Once the device is put in the configuration illustrated in FIG. 3A, it is a matter of attaching pedicle screw 2 in a corresponding vertebral body, by means of a maneuvering component cooperating with blind hole 8 of this pedicle screw 2.

As an assembly variant, it is possible to first of all attach each pedicle screw in a corresponding vertebral body. Then, each intermediate element 22 is introduced into interior volume 16 of mobile element 10, as explained in reference to FIG. 2.

The stationary element and the mobile element are then mutually brought together, intermediate element 22 is tilted within its housing 6. Then one brings closer intermediate element 22 thus tilted, with respect to pedicle screw 2, so that flat part 6 cooperates with the periphery of outlet 27, as illustrated in FIG. 3.

Once the device of the invention is placed in the configuration of this FIG. 3A, it is possible to connect, on flat part 6, a stop means which is advantageously removable, such as screw 32. The latter, by limiting the pivoting of head 4 with respect to intermediate element 22, keeps this head from regaining its position in FIG. 3, which prevents any disconnection between intermediate element 22 and pedicle screw 2.

Figure 4:
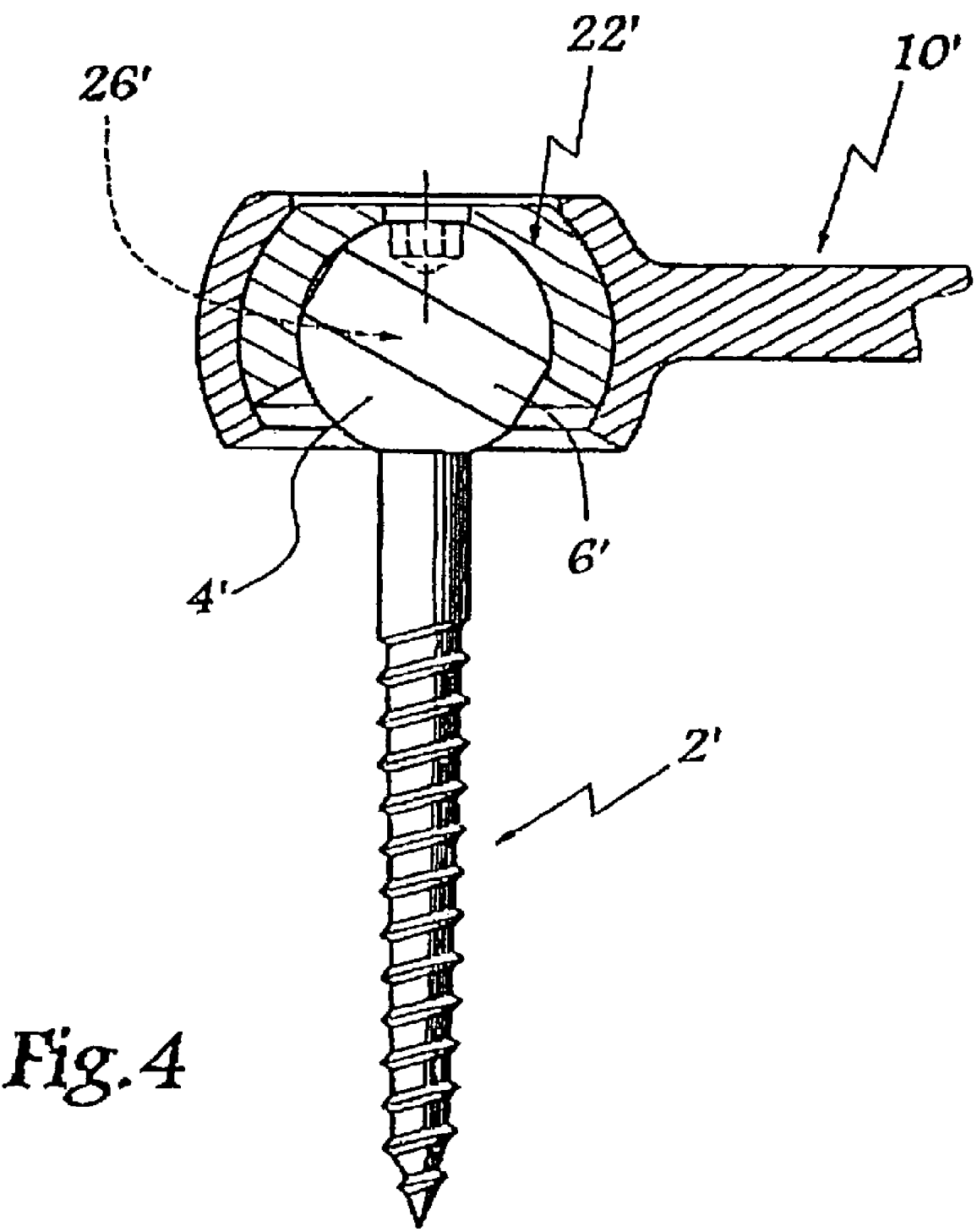
FIGS. 4 to 6 are views similar to FIG. 3A, illustrating embodiment variants of the device according to the invention.

FIG. 4 illustrates an embodiment variant of the invention, in which pedicle screw 2' is provided with spherical head 4' which is itself provided with inclined equatorial flat part 6'. This head 4' is introduced, in a manner similar to that described in the preceding, into intermediate element 22' provided with interior volume 26'.

It should be noted that, contrary to the example described in reference to FIGS. 1 to 3, spherical head 4' and interior volume 26' are concentric. In other respects, intermediate element 22' is received in interior volume 16' of mobile element 10' in a manner similar to that described above.

Figure 5A:
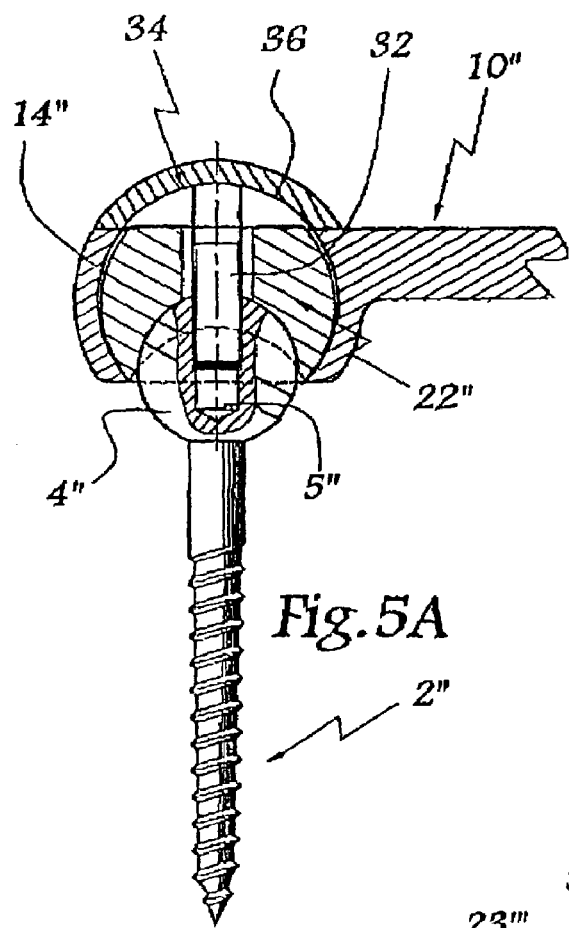
Figure 5B:
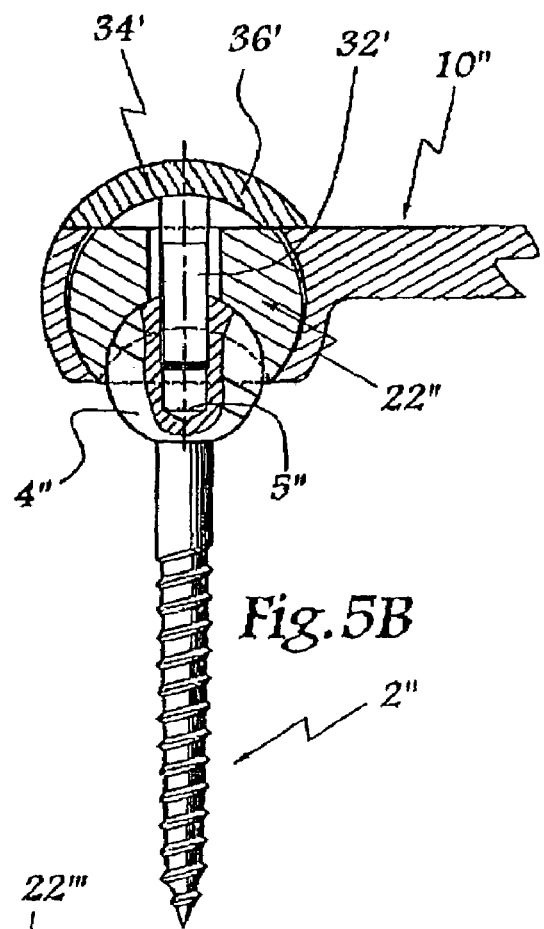

FIGS. 5 and 5A illustrate embodiment variants in which removable attachment means are provided, allowing one to connect pedicle screw 2" either with mobile element 10" or with intermediate element 22". To this effect, head 4" of the pedicle screw is provided with threading 5", cooperating with threaded rod 32 of attachment element 34. The latter also has dome 36 in the shape of a mushroom, which rests on the walls of end 14" of mobile element 10".

In the embodiment of FIG. 5A, dome 36' of attachment element 34' also rests on the end of intermediate element 22", while threaded rod 32' is connected with spherical head 4" of the pedicle screw.

Figure 6:
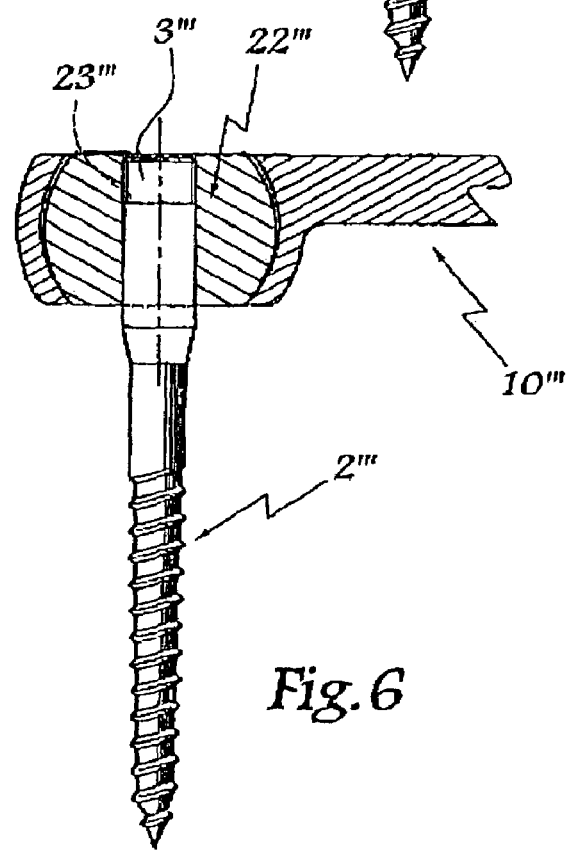

FIG. 6 illustrates an additional variant of the invention, in which intermediate element 22''' is hollowed with threading 23'''. The latter cooperates with threaded end 3''' of pedicle screw 2''', which has no spherical head. Intermediate element 22''' is in other respects received, in the manner of a ball and socket joint, in mobile element 10''' as in the preceding examples.

As a variant, it is possible to replace the pedicle screw described above by a rod extending from a sacral plate, namely a plate which is intended to be screwed on the sacrum.

FIGS. 7 and 8 illustrate another embodiment of the invention, which uses at least two pedicle screws 2, as well as at least two intermediate elements 22, identical to those described in reference to FIGS. 1 to 3.

Mobile element 110 has tubular body 112 which is ended by two closed ends 114 and is hollowed with first longitudinal notch 120 whose periphery is essentially rigid, allowing each intermediate element 22 to be introduced into interior volume 116 of mobile element 110.

This introduction is carried out in a manner similar to that described in reference to FIGS. 2, 2A and 2B, by pivoting of the intermediate element a quarter turn. Provided furthermore is a second longitudinal notch 120' diametrically opposite the one 120, allowing passage of a maneuvering component, for the purpose of attachment of each screw 2 in the corresponding vertebrae.

This embodiment gives three degrees of freedom in rotation to intermediate element 22 with respect to mobile element 110, and also allows axial sliding of this intermediate element along cylindrical body 112. As a variant, head 4 of each screw can be concentric with respect to the intermediate element, as in the embodiment example described in reference to FIG. 4.

Figure 9:
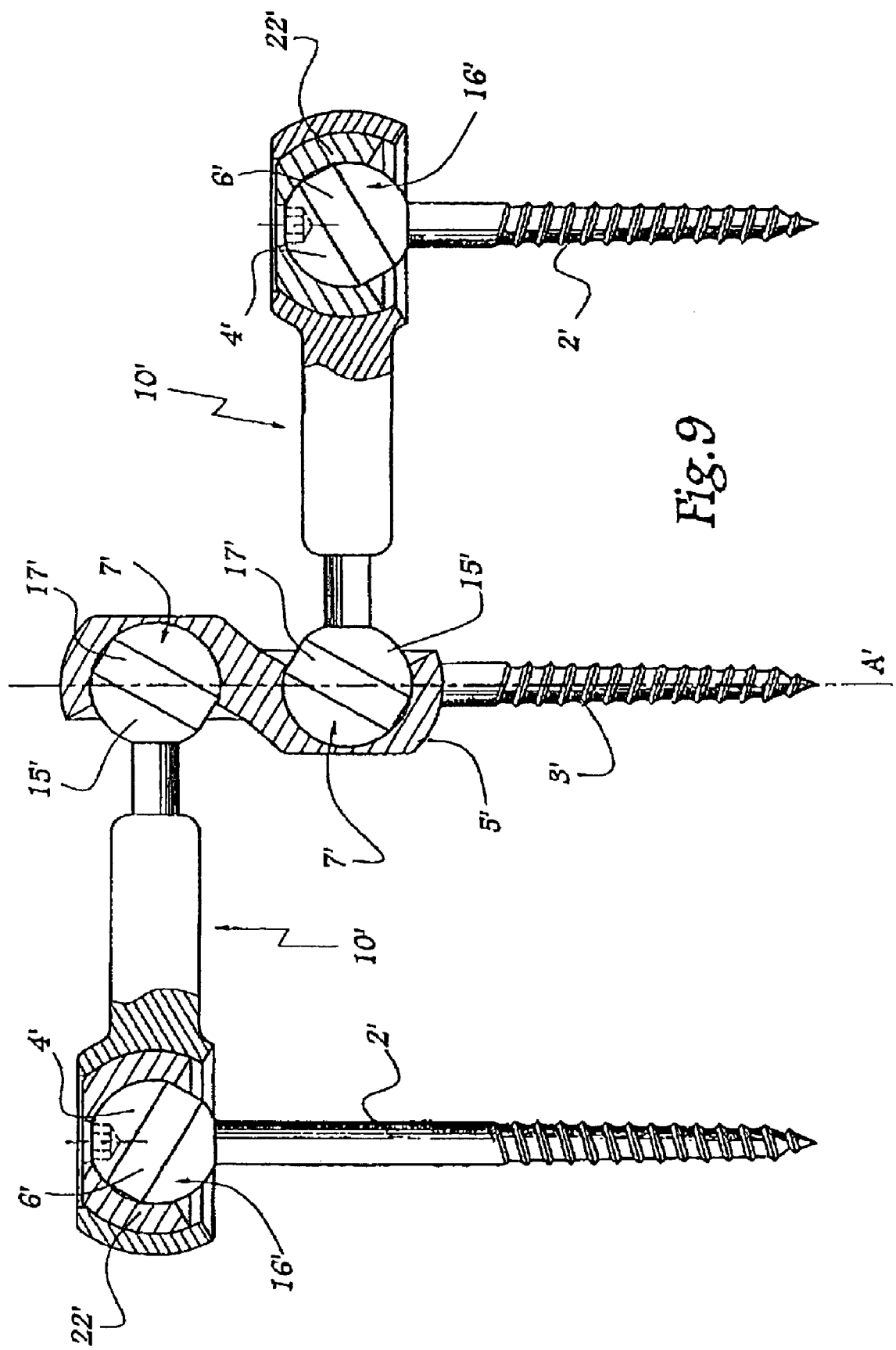
FIGS. 9 and 10 are views in longitudinal section, illustrating two additional embodiment variants of the invention.

FIG. 9 illustrates a device allowing one to connect three neighboring vertebrae.

This device includes two end screws 2', similar to those of FIG. 4. Each screw has head 4' provided with flat part 6', cooperating with intermediate element 22'. The latter is received in interior volume 16' of mobile element 10', which is ended, opposite from its end which receives intermediate element 22', by spherical head 15'.

Provided furthermore is additional screw 3', placed in middle position. It has elongated head 5', in which two housings 7' are arranged, of which the truncated spherical walls extend according to an angular sector greater than 180°.

These two housings are open on opposite sides from one another, in a manner roughly perpendicular to the main axis of this screw 3'. The transverse dimension of the outlet of each housing 7' is less than the diameter of its spherical walls. Spherical head 15' of each mobile element 10', which is provided with inclined equatorial flat part 17', cooperates with one of housings 7' of middle screw 3'.

For the purpose of assembling the prosthesis, it is first of all a matter of introducing each spherical head 15' into the interior volume of a corresponding housing 7', as described in the preceding for the introduction of head 4 of screw 2 in the interior volume of intermediate element 22'.

Then, each intermediate element 22' is introduced into the interior volume of mobile element 10'. Finally, head 4' of each end screw 2' is introduced into the interior volume of a corresponding intermediate element 22'.

Figure 10:
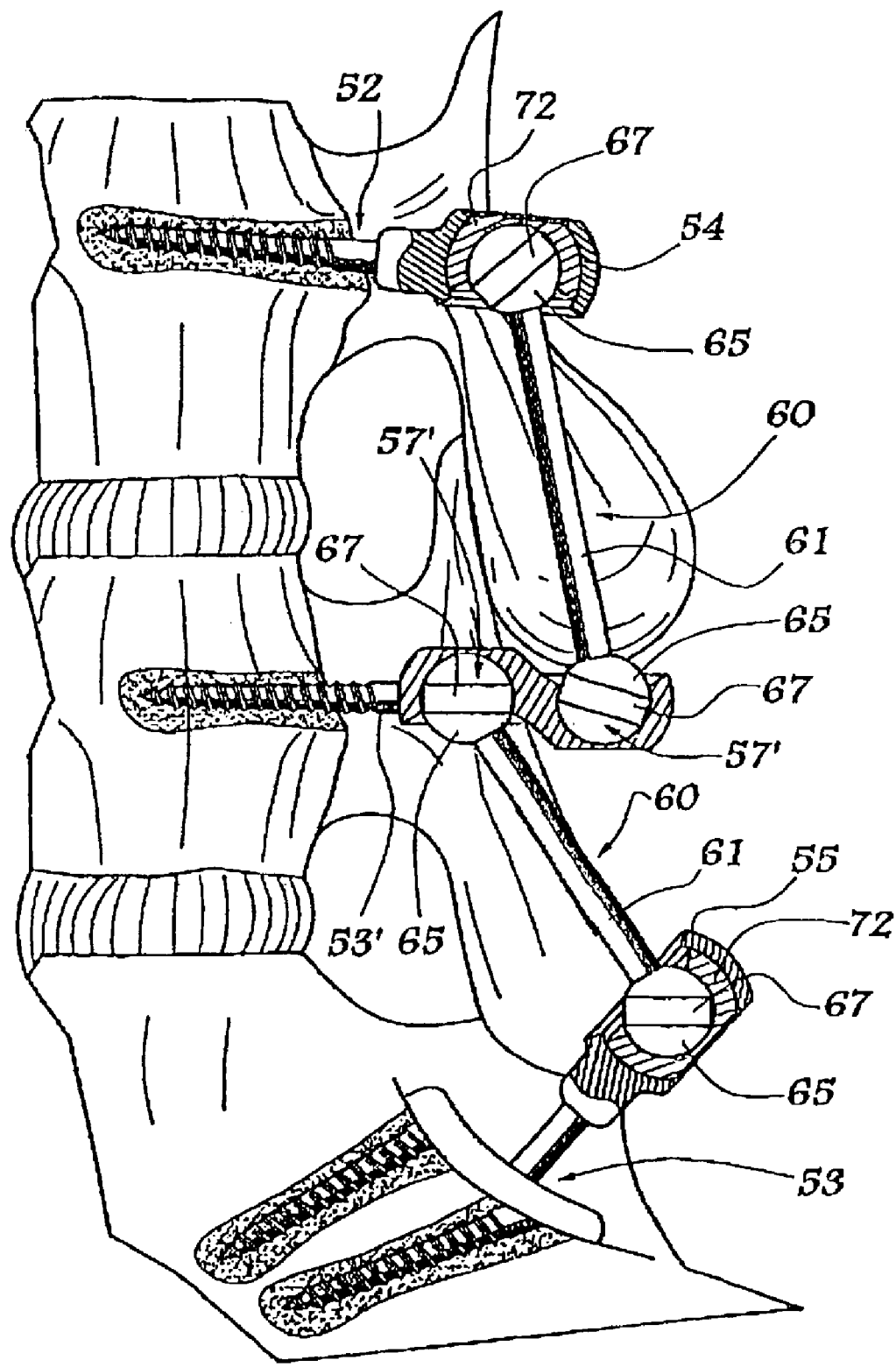

FIG. 10 illustrates a device allowing one to connect two neighboring vertebrae, as well as the sacrum.

Two similar mobile elements 60 are provided, each of which includes rod 61. The latter is ended, at its two ends, by spherical head 65 provided with inclined flat parts 67.

Middle screw 53' similar to that 3' of FIG. 9 is furthermore provided. Each spherical head 65 is received in corresponding housing 57' belonging to this middle screw 53'.

Furthermore, two stationary end elements are provided, namely pedicle screw 52, as well as plate 53, attached on the sacrum. At its opposite end from middle screw 53', each mobile element 60 is received in intermediate element 72, similar to those 22, 22'; 22" and 22"' described above.

Furthermore, this intermediate element 72 is received in the interior volume of head 54, 55, respectively belonging to pedicle screw 52 or to sacral plate 53.

The mutual connection between head 65, intermediate element 72, and screw 52 or plate 53 is similar to that existing between, for example, head 4 of screw 2, intermediate element 22 and mobile element 10.

In other words, in this FIG. 10, head 65 is substituted for head 4, the interior volume of screw 52 or plate 53 is substituted for the interior volume of mobile element 10, while intermediate element 72 ensures the articulation of mobile element 60 and of screw 52, just as intermediate element 22 ensures the articulation of screw 2 and of mobile element 10.

Figure 11:
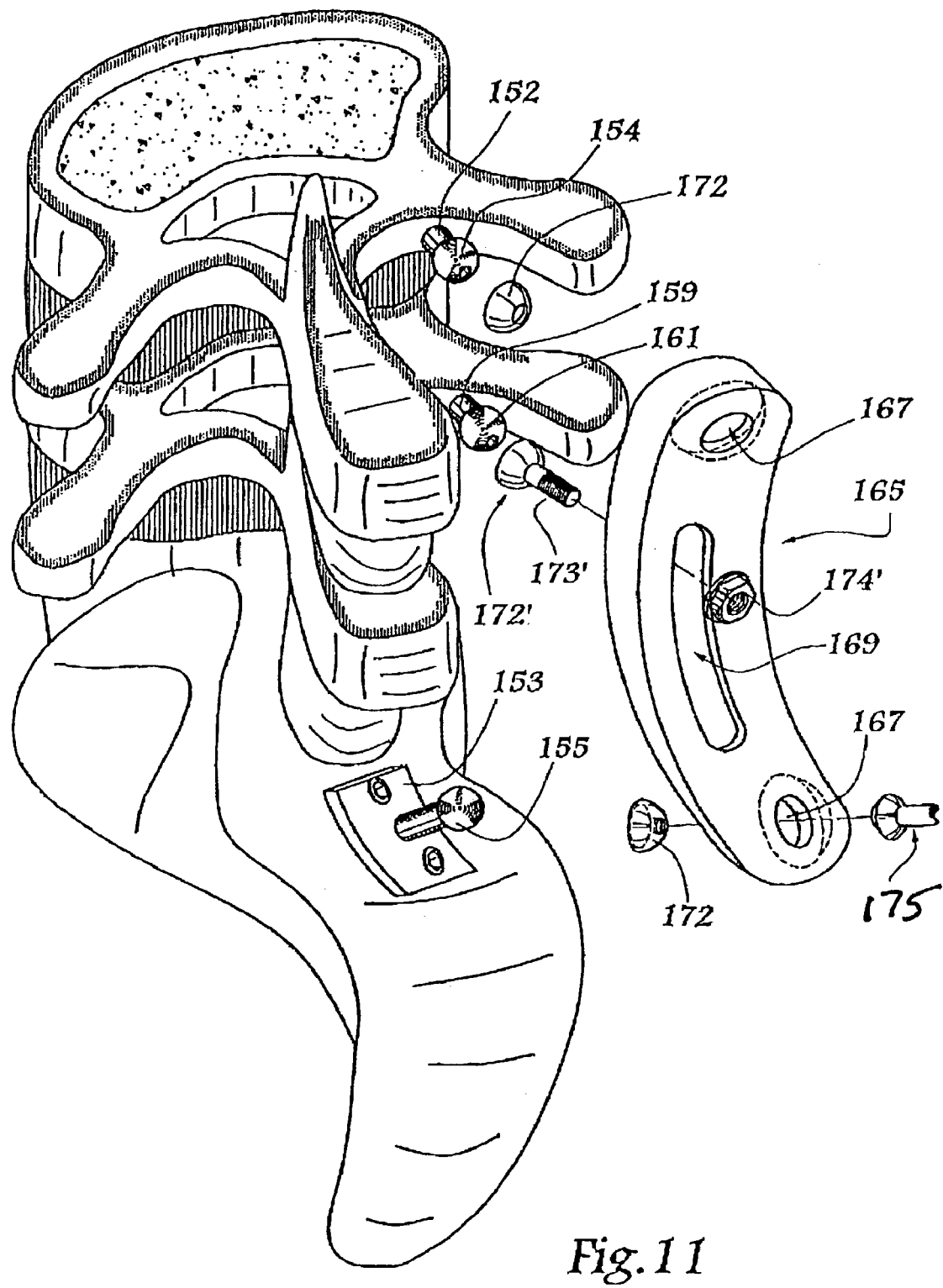
FIG. 11 is a perspective view, illustrating the different elements of a device according to an additional variant of the invention.
Figure 12:
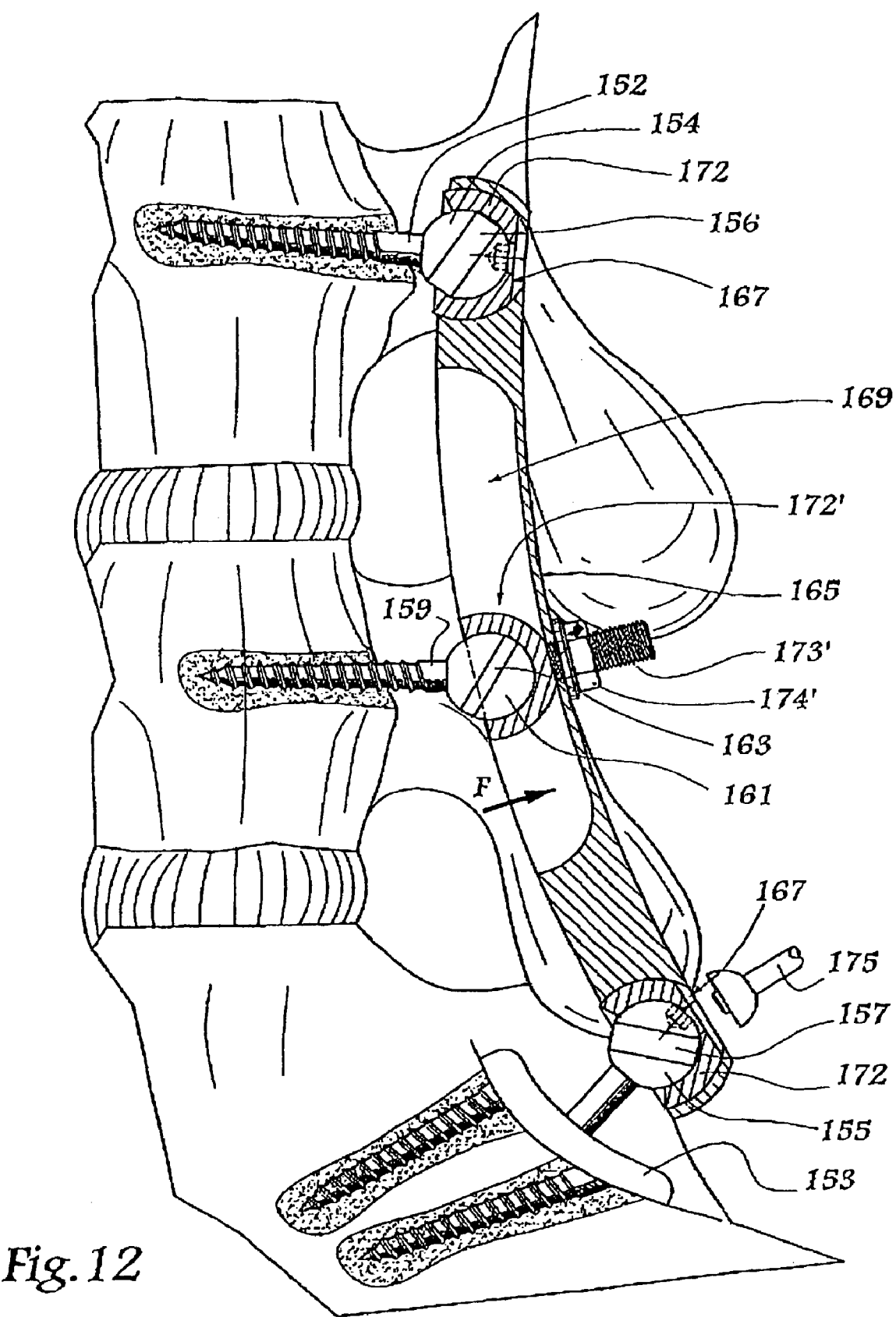
FIG. 12 is a view in longitudinal section of the device of FIG. 11, once assembled.

FIGS. 11 and 12 illustrate a device allowing one to mutually connect two lumbar vertebrae, as well as the sacrum.

This device has upper pedicle screw 152, ended by spherical head 154 provided with inclined flat part 156. Provided furthermore is sacral plate 153, ended by spherical head 155 provided with inclined flat part 157. This device also has middle screw 159 ended by spherical head 161 provided with inclined equatorial flat part 163.

Also provided is elongated plate 165, of which each end is hollowed with corresponding cavity 167. Each cavity is similar to housing 16 represented in FIG. 1. This elongated plate 165 is furthermore hollowed with oblong opening 169.

Head 154, 155 of end screw 152 or of plate 153 is received in corresponding cavity 167, with insertion of intermediate element 172, similar in particular to that 22. Head 161 of middle screw 159 is received in the interior volume of intermediate element 172', which differs from that 172, in the sense that it is provided, opposite from its outlet, with threaded rod 173', which is capable of cooperating with nut 174'.

The assembly of the device of FIGS. 11 and 12 will now be explained.

It is first of all a matter of introducing each intermediate element 172 into corresponding cavity 167, as described in reference to FIGS. 2 to 2B. Then, elongated plate 165 is brought towards screw 152 and sacral plate 153.

Heads 154, 155 are then introduced into the interior volume of each intermediate element 172. For this purpose, it can be wise to pivot these intermediate elements without moving in translation elongated plate 165, with respect to screw 152 and plate 153. This can be done by the intermediary of compression device 175, whose end passes through the opening of cavity 167 opposite from the vertebrae.

It should be noted that before elongated plate 165 is moved towards the vertebrae, intermediate element 172' has been placed on spherical head 161 of middle screw 159. Rod 173' of this intermediate element then passes through opening 169 of the plate. It is thus possible, by screwing of nut 174' on threaded rod 173', to move, with respect to elongated plate 165, middle screw 159 according to arrow F. This is particularly advantageous inasmuch as it allows one to induce a movement of the last lumbar vertebra according to this arrow F, that is to say "to pull" this vertebra.

Figure 13:
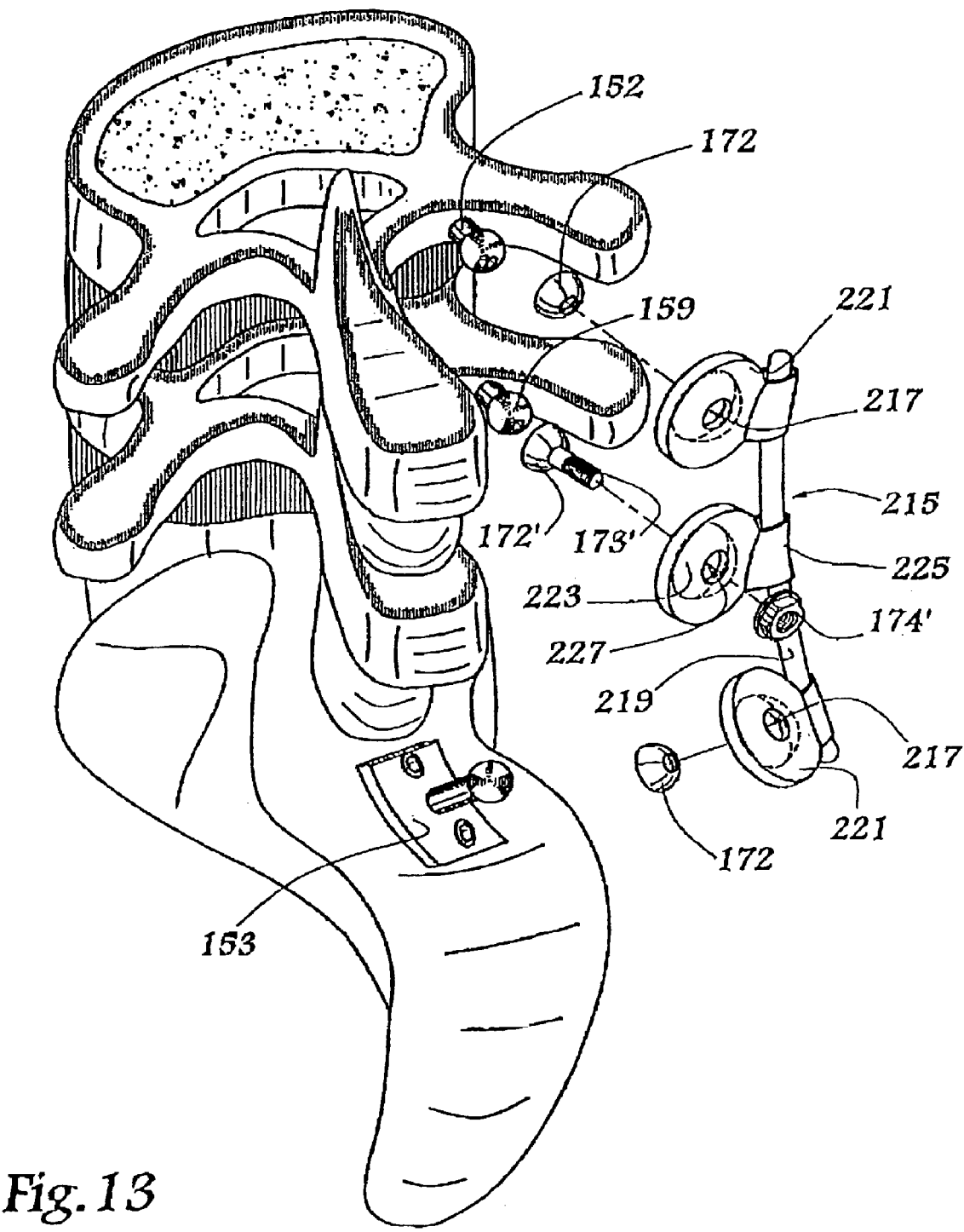
FIGS. 13 to 15 are perspective views, similar to FIG. 11, illustrating three additional embodiment variants of the invention.

FIG. 13 illustrates an additional embodiment variant of the invention, in which elongated plate 165 is replaced by connecting component 215, which has rod 219 ended by two disks 221, each of which is provided with cavity 217, similar to those 167.

Provided furthermore is intermediate disk 223 which can be attached on rod 219 by collar 225. This disk 223 is hollowed with middle opening 227.

Each end disk 221 is capable of cooperating, with insertion of intermediate element 172, with screw 152 or sacral plate 153. Furthermore, threaded rod 173' of intermediate element 172' is capable of passing through opening 227 of intermediate disk 223, in a manner similar to oblong opening 169.

Figure 14:
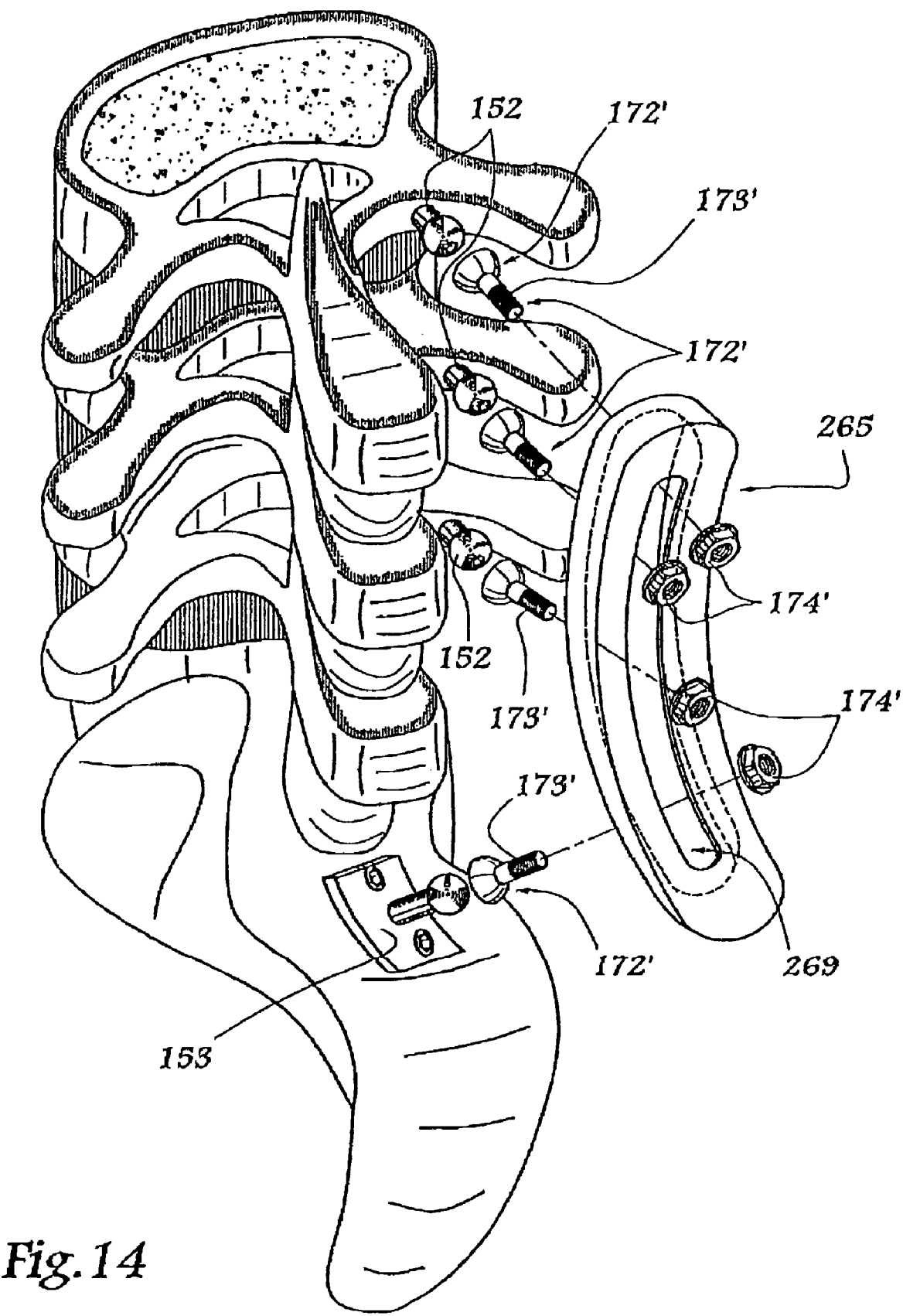

FIG. 14 illustrates an additional variant of the invention. Three pedicle screws 152, sacral plate 153, as well as elongated connecting plate 265 are provided. The spherical head of each screw 152 or of plate 153 is received in the interior volume of corresponding intermediate element 172'.

Furthermore, each threaded rod 173' of corresponding intermediate element 172' is capable of penetrating into opening 269 of plate 265, in such a way as to cooperate with corresponding nut 174'.

Figure 15:
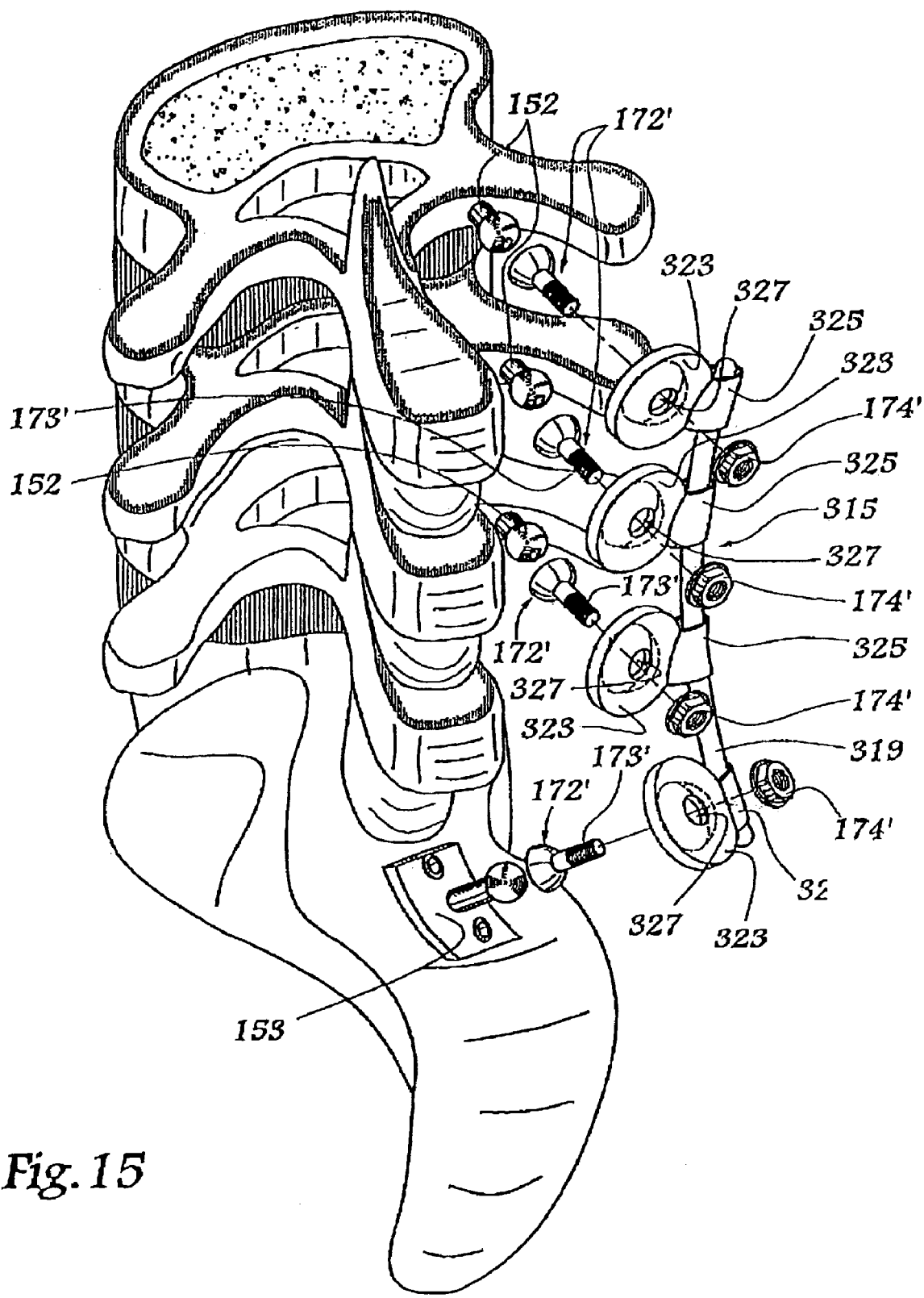

FIG. 15 illustrates a last embodiment variant of the invention.

Connecting component 315 is provided, which has rod 319 on which disks 323 are arranged, which can be attached by means of collars 325.

Opening 327 of each disk 323 is capable of receiving threaded rod 173' of intermediate element 172', which cooperates with the spherical head of screw 152, or else of sacral plate 153. Each rod 173' is furthermore capable of receiving nut 174'.

The invention allows one to accomplish the objectives mentioned in the preceding.

In effect, the different elements constituting the intervertebral connecting device of the invention have a relatively simple structure.

The assembly of these elements is particularly and can be done by a surgeon without his having to use great physical force.

The assembly of the different elements of the connecting device of the invention furthermore induces almost no deformation of these elements, which is advantageous in terms of mechanical reliability.

It should be noted that the presence of the intermediate element allows mutual assembly of the stationary element and the mobile element, even when there is practically no clearance in terms of rotation between these two elements.

Finally, once the intervertebral connecting device of the invention is assembled, it has a great resistance with regard to mechanical stresses, exerted in traction in particular. In effect, the presence of the intermediate element allows the possible forces to which the connecting device according to the invention is subjected to be transmitted only to a very slight degree.

What is claimed is:

1. An intervertebral connecting device, which is intended to connect at least two vertebrae together, this device being characterized in that it includes:
   at least one stationary element, connectable to a vertebra or the sacrum and including a head portion,
   at least one mobile connecting element capable of moving with respect to the at least one stationary element, said at least one mobile connecting element extending between an external upper surface and an external lower surface and including an opening extending through said external lower surface, said opening configured to facilitate passage of said head therethrough,
   at least one intermediate element having a ring shaped exterior allowing the articulation of the at least one mobile element with respect to the at least one stationary element,
   in that the intermediate element is received in a first interior volume of said mobile element,
   in that the stationary element is received at least partially in a second interior volume of the intermediate element,
   means for allowing a connection through translation of said stationary element with respect to said intermediate element, this means of connection in translation including the periphery of an outlet defined in the second interior volume of the at least one intermediate element.

2. A device according to claim 1, characterized in that said at least one intermediate element is also connected in rotation with respect to mobile element.

3. A device according to claim 1, characterized in that said at least one intermediate element has at least one degree of freedom, at least in translation, with respect to said first mobile element.

4. A device according to claim 3, characterized in that said mobile element has tubular portion, along which said intermediate element is capable of sliding.

5. A device according to claim 1, characterized in that the intermediate element or each intermediate element is received in an interior volume of stationary element, in that mobile element is received at least partially in an interior volume of the intermediate element, and in that some means are provided allowing the connection, at least in translation, of the mobile element with respect to the intermediate element.

6. The device of claim 1, wherein the ring shaped exterior of the intermediate element is arranged to cooperate with a corresponding spherical interior of the mobile connecting element to permit the articulation.

7. An intervertebral connecting device, comprising:
   a stationary element to engage a vertebra or a sacrum and including a head portion;
   a mobile element extending between an external upper surface and an external lower surface and including an opening extending through the external lower surface, the opening configured to facilitate passage of the head portion therethrough;
   an intermediate element having a truncated spherical exterior surface and being operable to be assembled between the stationary element and the mobile element to allow articulation of the mobile element with respect to the stationary element, the mobile element including a first interior volume to at least partially receive the intermediate element and the intermediate element including a second interior volume to at least partially receive the stationary element, to assemble the stationary element, the intermediate element and the mobile element together; and
   means for connecting the stationary element and intermediate element including the intermediate element having an outlet with a rigid periphery to engage the stationary element and restrict at least one degree of translational movement of the stationary element relative to the intermediate element when the stationary element, the intermediate element, and the mobile element are assembled together.

8. The device of claim 7, wherein the truncated spherical exterior surface of the intermediate element is arranged to cooperate with a corresponding spherical interior surface of the mobile element.

9. The device of claim 7, wherein the head portion is operable to be received in the second interior volume, the head portion, the first interior volume and the second interior volume being approximately concentric.

10. The device of claim 7, wherein the intermediate element has at least one degree of freedom with respect to the mobile element when assembled with the mobile element and the stationary element.

11. The device of claim 10, wherein the mobile element includes a tubular portion along which the intermediate element is capable of sliding when at least a portion of the intermediate element is received therein.

12. The device of claim 7, wherein the mobile element includes an arcuate notch in the external lower surface for introduction of the intermediate element in the first interior volume.

13. The device of claim 7, wherein the stationary element has at least one degree of freedom in rotation with respect to the intermediate element when assembled with the intermediate element and the mobile element.

14. The device of claim 7, wherein the head portion of the stationary element includes a spherical exterior surface arranged to engage a corresponding spherical interior surface of the intermediate element.

15. The device of claim 14, wherein the spherical exterior surface of the head portion of the stationary element is provided with a flat part to introduce the stationary element into the second interior volume of the intermediate element.

16. The device of claim 7, wherein the stationary element is connected with the intermediate element both in translation and in rotation when assembled together.

17. The device of claim 16, wherein the stationary element has a threaded end arranged to engage a threaded opening of the intermediate element.

18. The device of claim 7, wherein the stationary element is one of a pedicle screw operable to be attached to the vertebra and a plate operable to be attached to the sacrum.

19. An intervertebral connecting system, comprising:
at least two stationary elements each for engaging a vertebra or a sacrum;
at least two corresponding intermediate elements;
a connecting element to connect the at least two stationary elements;
wherein each of the intermediate elements is positionable between one of the stationary elements and the connecting element to allow articulation of the connecting element with respect to the stationary elements;
wherein each of the stationary elements includes an at least partially spherical head portion, and each of the intermediate elements includes an interior volume defined by at least partially spherical interior surfaces corresponding to the at least partially spherical head portions and configured to articulate with respect to the head portions;
wherein the connecting element defines at least two bottom opening holes to receive the at least two intermediate elements, the holes being configured to facilitate passage of the spherical head portions therethrough; and
means for connecting the stationary elements and the intermediate elements including the intermediate elements each having an outlet with a rigid periphery to engage the corresponding stationary element, the means further including the head portions of the stationary elements each having two opposing flat segments to permit the introduction of the head portions in the interior volumes of the intermediate elements at oblique angles.

20. The device of claim 19, wherein at least one of the intermediate elements includes a threaded post configured to be received through the corresponding hole in the connecting element and configured to mate with an internally threaded nut to secure the intermediate element to the connecting element.

21. An orthopedic implant apparatus, comprising:
a monolithic orthopedic screw having a shaft with a main axis and a head, said head being spherical with an equatorial flat part that is not perpendicular to said main axis;
a mobile element having a body that extends between two bone pieces and two hollow ends, each of said ends defining a respective interior volume having walls forming a truncated sphere of a first diameter, said walls including at least one arcuate notch on an external surface thereof for locally widening the respective end, said interior volume having an outlet with an edge defining a second diameter that is less than said first diameter;
an intermediate member having an exterior surface forming a portion of a sphere of diameter equal to said first diameter, said intermediate member having opposed planar surfaces and a hollow housing with a respective opening in each of said opposed planar surfaces, said housing having interior truncated spherical walls having a third diameter equal to the diameter of said head of said screw, and said openings respectively having a fourth diameter and a fifth diameter, each of which is less than said third diameter;
wherein said equatorial flat part of said screw has a width dimension that is equal to or smaller than said fourth diameter and said fifth diameter, and said intermediate member has a width dimension measured between said opposing pianar surfaces that is equal to or smaller than said second diameter of said outlet of said mobile element.

22. The apparatus of claim 21, wherein said screw head is in said interior volume of said mobile element, and said shaft of said screw extends through said outlet of said interior volume of said mobile element.

23. The apparatus of claim 22, wherein said intermediate member is within said interior volume of said mobile element, and said edge of said outlet retains said intermediate member within said mobile element.

24. The apparatus of claim 21, wherein said screw head can be inserted in said intermediate member housing only when said screw head is oriented so that its equatorial flat portion is adjacent one of said openings of said intermediate member.

25. The apparatus of claim 21, wherein said intermediate member can be inserted into one of said hollow ends only by turning said intermediate member so that said opposed planar surfaces face the edge of said outlet of said mobile element.

* * * * *